United States Patent [19]

Ogiso et al.

[11] Patent Number: 5,064,436
[45] Date of Patent: Nov. 12, 1991

[54] BONE PROSTHETIC MATERIAL

[75] Inventors: Makoto Ogiso; Tetsuro Ogawa; Takeshi Ichitsuka; Masahide Inoue, all of Tokyo, Japan

[73] Assignee: Asahi Kogaku Kogyo K.K., Tokyo, Japan

[21] Appl. No.: 373,708

[22] Filed: Jul. 3, 1989

Related U.S. Application Data

[63] Continuation of Ser. No. 55,083, May 28, 1987, abandoned.

[30] Foreign Application Priority Data

May 28, 1986 [JP] Japan ................................ 61-123132

[51] Int. Cl.$^5$ ................................................ A61F 2/28
[52] U.S. Cl. ......................................... 623/16; 623/16
[58] Field of Search ........................ 623/16, 18, 66, 23

[56] References Cited

U.S. PATENT DOCUMENTS

| 4,629,464 | 12/1986 | Takata et al. | 623/16 |
| 4,654,314 | 3/1987 | Takagi et al. | 623/16 X |
| 4,693,986 | 9/1987 | Vit et al. | 623/16 X |

FOREIGN PATENT DOCUMENTS 2142919A  1/1985  United Kingdom .

*Primary Examiner*—David J. Isabella
*Assistant Examiner*—G. Gualtieri
*Attorney, Agent, or Firm*—Sughrue, Mion, Zinn, Macpeak & Seas

[57] ABSTRACT

A bone prosthetic material composed of calcium phosphate group granules which have open cells with an average pore size of $0.01-(10\ \mu m)^2$ over a surface density of at least one per $10\ \mu m^2$. The prosthetic material is prepared by mixing organic inflammable particles with a calcium based powder, granulating and then firing the mixture.

5 Claims, 3 Drawing Sheets

BONE PROSTHETIC MATERIAL

This is a continuation of application Ser. No. 07/055,083 filed May 28, 1987 now abandoned.

BACKGROUND OF THE INVENTION

1. Field of the Invention

The present invention relates to a bone prosthetic material (filler) which is useful in oral surgery, orthopedic surgery and other fields for the purpose of filling the part of a bone which has been removed such bone removal may result from an operation on bone tumor, pyorrhea alveolaris or other diseases. The present invention also relates to a process for producing such a bone prosthetic material.

2. Background of the Invention

Bone prosthetic materials of the type contemplated by the present invention have heretofore been used in the form of blocks, granules or some other shapes that are formed of metals (e.g., cobalt-chromium alloys, titanium, and stainless steel), ceramics (e.g., alumina, zirconia, tricalcium phosphate, hydroxyapatite, and calcium phosphate-based glass), high-molecular weight materials (e.g., silicone resins) and carbon.

Of these materials, those which are based on a calcium phosphate group such as tricalcium phosphate, hydroxyapatite and calcium phosphate-based glass have been the subject of the most intensive studies in recent years because they are very similar to bones in composition and exhibit an extremely high degree of biocompatibility. However, even bone prosthetic materials made of such calcium phosphate group based materials are "foreign" to living tissues and their ability to coalesce with a new growth of bone is limited to the area which is close to the living tissues of interest. In areas distant from such living tissues the prosthetic material is subjected to a so-called encapsulating reaction in which the prosthetic material is surrounded by fibrous tissue and becomes excessively soft. Therefore, in areas where the healing process is inactive, even the bone prosthetic materials made from calcium phosphate materials fail to display good biocompatibility with the body tissues because of their encapsulation in a fibrous tissue.

Unexamined Published Japanese Patent Application No. 21763/1985 discloses an artificial bone material that is composed of sintered hydroxyapatite having open cells with sizes of 10-100 $\mu$m and a flexural strength of at least 100 kg/cm$^2$. However, this artificial bone material has to sacrifice the porosity in order to attain a flexural strength of at least 100 kg/cm$^2$, and the number of open cells it has is too small to effectively prevent encapsulation in a fibrous capsule.

SUMMARY OF THE INVENTION

An object of the present invention is to provide a bone prosthetic material that is capable of coalescing with a new growth of bone without undergoing encapsulation in a fibrous capsule even if it is at a site which is distant from living tissues and where the healing process is inactive.

Another object of the present invention is to provide a process for producing such an improved bone prosthetic material.

The invention can be summarized as a bone prosthetic material composed of porous calcium phosphate in granular form. The granules have open cells with an average pore size of 0.01-10 $\mu$m.

DETAILED DESCRIPTION OF THE PREFERRED EMBODIMENTS

Figure 1:
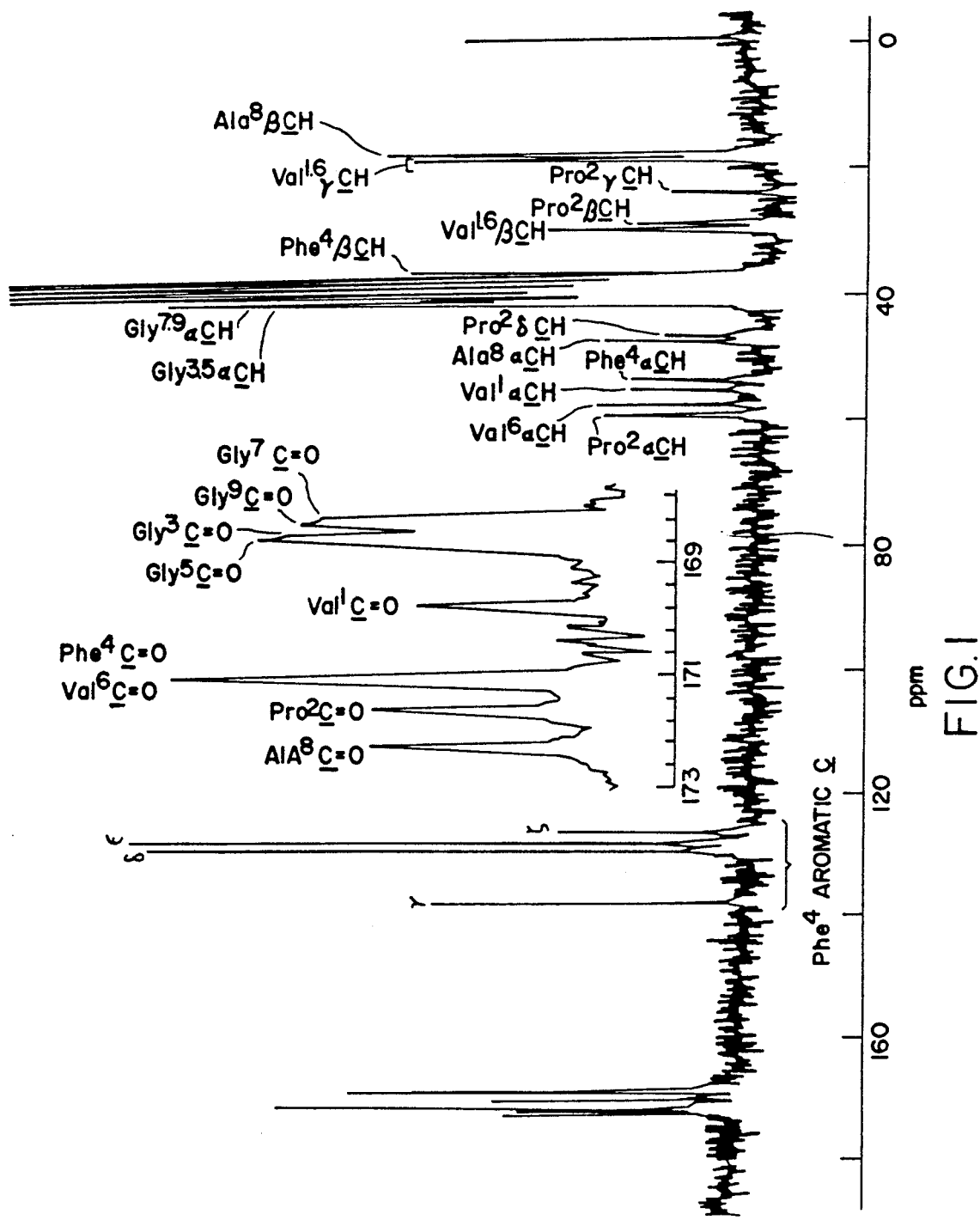
FIG. 1 is an electron micrograph ($\times$100) showing the structure of a granule in the bone prosthetic material prepared in the example of the present invention.
Figure 2:
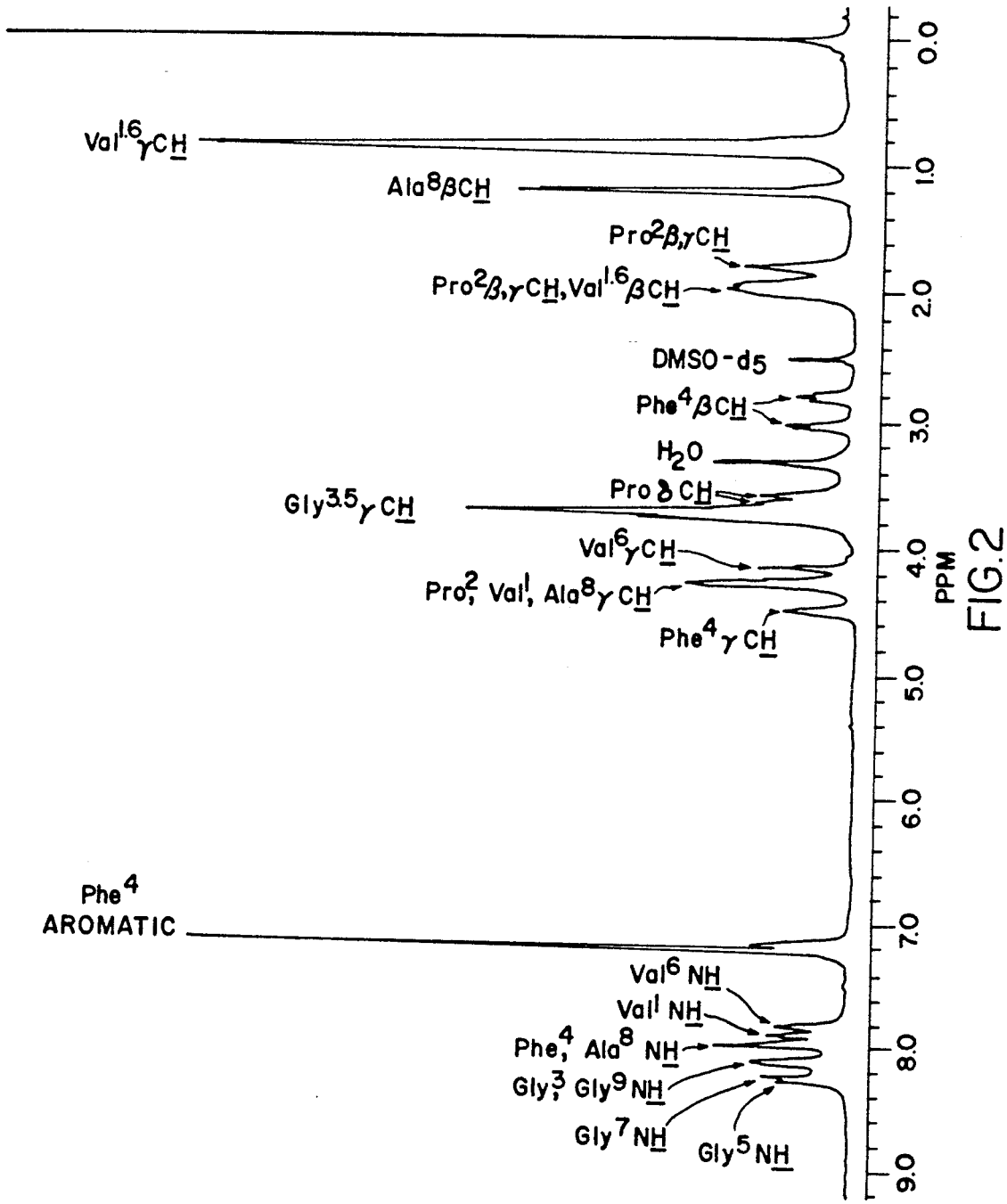
FIGS. 2 and 3 are electron micrographs showing the same granular structure but at different magnifications of 1,000 and 10,000.

The bone prosthetic material provided by the present invention is composed of porous calcium phosphate group based granules having open cells with an average pore size of 0.01-10 $\mu$m.

According to the present invention, this bone prosthetic material is produced by a process which comprises the steps of mixing a calcium phosphate powder with organic inflammable particles having an average size of 0.01-10 $\mu$m, granulating the resulting mix, and firing the granulation.

Encapsulation of the bone prosthetic material brought into the living body is induced by macrophages that adhere to the prosthetic material and identify it as foreign matter. The present inventors conducted a close study of this phenomenon and found that if there is a passage of body fluids at the site of the bone prosthetic material to which macrophages have adhered, the prosthetic filler will not be considered to be foreign matter by the macrophages and will not undergo encapsulation in a fibrous tissue.

The present invention has been accomplished on the basis of the fact that by forming open cells in a bone prosthetic material, passages for body fluids into the interior of the prosthetic material are provided and its encapsulation in fibrous tissues is prevented so as to promote its coalescence within a new growth of bone. In order that the bone prosthetic material will not be identified as foreign matter by macrophages, the pore size of the open cells in the prosthetic material is important and specifically they should not be excessively larger than the macrophages.

To meet this requirement, the bone prosthetic material of the present invention is provided with open cells having an average pore size of more than 0.01 pm but less than 10 $\mu$m. This average pore size range will be denoted as 0.01-10 $\mu$m. It is difficult to produce a bone prosthetic material with open cells having an average pore size of less than 0.01 $\mu$m. In addition, body fluids have limited access to such excessively small cells and satisfactory prevention of encapsulation cannot be achieved. Cells having an average pore size exceeding 10 $\mu$m are too much larger than macrophages to provide for the passage of body fluids at the site to which macrophages will adhere and it is also difficult to achieve satisfactory prevention of encapsulation of the bone prosthetic material.

In a preferred embodiment of the present invention, the granules of which the bone prosthetic material is composed have, on average, at least one open cell with an average pore size of 0.01-10 $\mu$m within a surface area of (10 $\mu$m)$^2$. If this requirement is met, the open cells having an average pore size within the specified range are distributed at such a density as to increase the probability that open cells will be situated at the site where macrophages are to adhere and thereby ensure prevention of encapsulation in a more effective way.

In another preferred embodiment of the present invention, the open cells in the bone prosthetic material granules have an average pore size of 0.01–1 μm. If this condition is met, macrophages that adhere to open cells will bridge them to ensure even better results in prevention of encapsulation.

In still another preferred embodiment of the present invention, the bone prosthetic material granules have a porosity of 60–90%. If the porosity is less than 60%, the desired open cells are not easily formed and no satisfactory passage of body fluids will by provided. If the porosity exceeds 90%, there is a high likelihood that the resulting granules have reduced strength and are friable.

In the present invention, the granules of which the bone prosthetic material is composed are not limited in any particular way as regards their shape and they may have a spherical or anomalous shape. In order to provide for ease in the filling operation, the granules preferably have an average size of 0.1–1 mm. If the granules have an average size of less than 0.1 mm, they will be readily displaced by flowing body fluids. If the average size of the granules exceeds 1 mm, too many or excessively large gaps will form between granules to prevent effective coalescing to a new growth of bone.

Any of the known calcium phosphate group based materials may-be used in the present invention to make a powder which is to be mixed with organic inflammable particles in the manufacture of the claimed bone prosthetic material. Particularly preferable calcium phosphate group based materials include hydroxyapatite and tricalcium phosphate. The calcium phosphate powder made of these materials is composed of particles which typically have an average size of from about 1 to about 10 μm. Such particles may be ground in a ball mill or some other suitable device into fine particles having an average size of from about 0.05 to about 1 μm.

The organic inflammable particles may be in the form of beads of synthetic resins such as polystyrene, polyvinyl alcohol and polypropylene. Alternatively, they may be prepared by finely divided cellulose, animal fibers or other fibrous materials. In order to form open cells having an average pore size of 0.01–10 μm, the organic inflammable particles are required to have an average size within the same range.

In granulating a mix of the calcium phosphate group based powder with the organic inflammable particles, water, polyvinyl alcohol or some other appropriate material may optionally be added as a binder. The mix as the starting material preferably contains 30–70 parts (wt%) of the organic inflammable particles for 100 parts (wt%) by weight of the calcium phosphate group based powder. If the content of organic inflammable particles is less than 30 wt%, no satisfactory porosity is attained in the prosthetic granules. If the content of organic inflammable particles exceed 70 wt%, the resulting prosthetic granules have such a high porosity that their strength will be decreased.

Various methods may be employed to make a granulation. One method consists of mixing a calcium phosphate powder with the organic inflammable particles to form a slurry which is then dried to form a block that is subsequently ground into fine particles. Another method is to employ a pan type granulator.

The granulation thus prepared is then fired. While there is no particular limitation on the conditions that can be employed in firing the granulation, the following procedure is recommended. The granulation is heated from room temperature to about 600° C. at a rate of about 50° C./hr so as to burn away the organic inflammable particles. The granulation is subsequently heated up to about 1200° C. at a rate of about 100° C./hr and held at that temperature for about 8 hours so as to produce a sinter.

The bone prosthetic material produced by the method described above may be used in the following manner. After being sterilized, the filler is mixed with a sterile physiological saline solution and the resulting mix is charged into the lost part of a bone. The charged prosthetic material will coalesce to the surrounding bone tissue via a new growth of bone and thereby fill the lost part of the bone.

A ball mill was charged with 600 g of a synthetic hydroxyapatite powder (particle size: 1–10 μm), 400 g of polystyrene beads "Fine Pearl" (trade name of Sumitomo Chemical Co., Lt.; average particle size, 6 μm) and 2000 ml of distilled water the ball mill was operated for 24 hours to make a slurry of hydroxyapatite having an average particles size of 0.6 μm. The slurry was put in a petri dish which was placed in an oven with internal air circulation for 24 hours at 100° C. so as to dry the slurry into a block. The dry block was pulverized in a mortar into granules (100–1000 μm) which were fired in an electric furnace under the following conditions: heating from room temperature to 600° C. at a rate of 50° C./hr; subsequent heating from 600° C. to 1200° C. at a rate of 100° C./hr; holding at 1200° C. for 8 hours; and cooling at a rate of 200° C./hr.

The fired hydroxyapatite granules were sieved to a size range of 300–500 μm by passage through a stainless steel screen.

Figure 3:
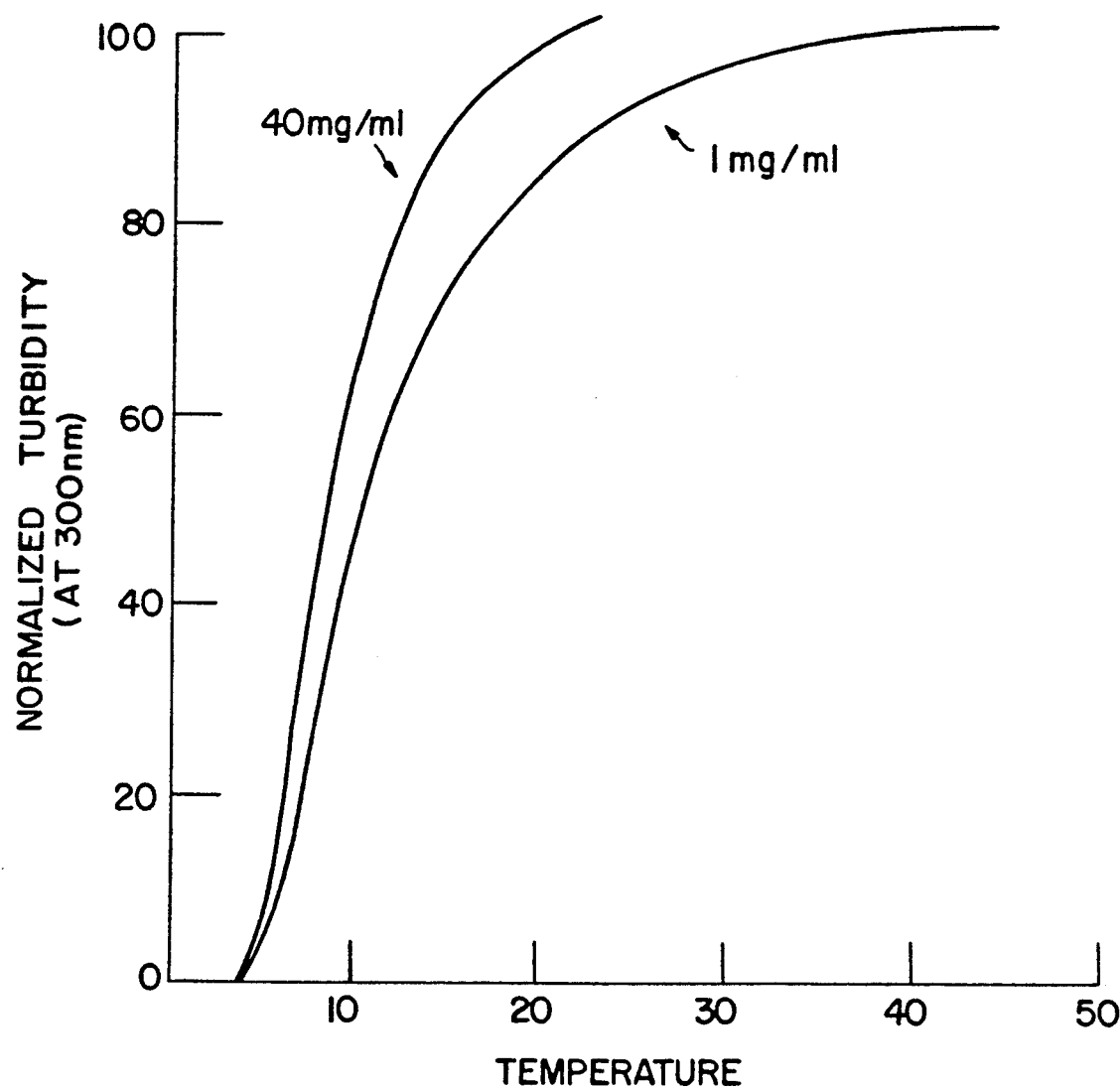

The bone prosthetic material made of the so prepared granule had open cells having an average pore size of about 4 μm. Electron micrographs of a single granule in this prosthetic material are reproduced in FIG. 1 (×100), FIG. 3 (×10,000).

As described in the foregoing pages, the bone prosthetic material of the present invention is composed of porous calcium phosphate group based granules having open cells with an average pore size of 0.01–10 μm. The granules of which this filler is made permit the passage of body fluids at the site of adhesion of macrophages and will not be recognized as foreign matter by adhering macrophages. This provides for effective prevention against encapsulation of the granules in fibrous tissues and thereby promote the coalescing of the granules to a new growth of bone and, hence, the healing process of the treated area.

What is claimed is:

1. A bone prosthetic material composed of porous calcium phosphate group based granules having homogeneous sized open cells with an average pore size of 0.01–10 μm, wherein said granules have on average at least one of said open cells within a surface area of (10 μm)$^2$ and the cells are homogeneously distributed and in direct contact with one another.

2. A bone prosthetic material according to claim 1, wherein said granules have an average size of 0.1–1 mm.

3. A bone prosthetic material according to claim 1, wherein said granules have a porosity of 60–90%.

4. A bone prosthetic material according to claim 1, wherein said calcium phosphate group granules comprise hydroxy apatite.

5. A bone prosthetic material according to claim 1, wherein said calcium phosphate group granules comprise tricalcium phosphate.

* * * * *